(12) United States Patent
Van Osch et al.

(10) Patent No.: US 11,183,355 B2
(45) Date of Patent: Nov. 23, 2021

(54) X-RAY TUBE

(71) Applicant: Malvern Panalytical B.V., Almelo (NL)

(72) Inventors: Jaap Van Osch, Almelo (NL); Jan-Pieter Chan, Almelo (NL)

(73) Assignee: MALVERN PANALYTICAL B.V., Almelo (NL)

(*) Notice: Subject to any disclaimer, the term of this patent is extended or adjusted under 35 U.S.C. 154(b) by 0 days.

(21) Appl. No.: 16/729,889

(22) Filed: Dec. 30, 2019

(65) Prior Publication Data
US 2020/0211807 A1 Jul. 2, 2020

(30) Foreign Application Priority Data
Dec. 31, 2018 (EP) .................................... 18215994

(51) Int. Cl.
*H01J 35/08* (2006.01)
*H01J 35/06* (2006.01)
*A61B 6/00* (2006.01)

(52) U.S. Cl.
CPC .............. *H01J 35/08* (2013.01); *H01J 35/06* (2013.01); *A61B 6/582* (2013.01); *H01J 2235/086* (2013.01)

(58) Field of Classification Search
CPC ...... H01J 35/08; H01J 35/06; H01J 2235/086; H01J 35/066; H01J 35/14; H01J 35/16; H01J 35/24; A61B 6/582
See application file for complete search history.

(56) References Cited

U.S. PATENT DOCUMENTS

| 2010/0150315 A1 | 6/2010 | Filmer et al. | |
| 2014/0124905 A1* | 5/2014 | Decker | H01L 29/0619 257/656 |
| 2017/0076904 A1* | 3/2017 | Hanaki | H01J 35/18 |
| 2017/0290135 A1* | 10/2017 | Shimizu | H01J 35/064 |

FOREIGN PATENT DOCUMENTS

| JP | 2010 033992 | 2/2010 |
| JP | 2010 055883 | 3/2010 |

* cited by examiner

*Primary Examiner* — Marcus H Taningco
(74) *Attorney, Agent, or Firm* — Leason Ellis LLP

(57) ABSTRACT

The present invention relates to an X-ray tube for X-ray analysis. The X-ray tube comprises an anode having a target surface and a cathode. The cathode comprises an emission loop. The emission loop extends around an axis that passes through the anode, and the cathode and the anode are spaced apart from one another along the axis. Electrons emitted from the cathode irradiate the target surface of the anode to produce X-rays. The X-ray tube further comprises an electron beam guide. The electron beam guide is configured to guide electrons emitted by the cathode, so as to irradiate an area of the anode. The irradiated area is enclosed by a single boundary.

15 Claims, 6 Drawing Sheets

X-RAY TUBE

CROSS-REFERENCE TO RELATED PATENT APPLICATIONS

The present application claims priority under 35 U.S.C. § 119 to European Patent Application No. 18215994.7, filed Dec. 31, 2018, the entire contents of which is incorporated by reference herein as if expressly set forth in its respective entirety herein.

FIELD OF THE INVENTION

The present invention relates to an X-ray tube.

BACKGROUND OF THE INVENTION

X-rays are generated by an X-ray source, often in the form of a vacuum tube including a cathode and an anode (i.e. an X-ray tube). Electrons from the cathode are accelerated towards the anode by an electric field and generate X-rays on collision with the anode. These X-rays pass out of the X-ray tube through a window. A high voltage (for example, in the range of 1 kV to 100 kV) is applied to the anode, while the cathode is kept at ground. That is, there is a high potential difference between the anode and the cathode of the X-ray tube.

The current associated with the beam of electrons emitted from the cathode and directed towards the anode is called the emission current. In general, the higher the emission current, the higher the number of electrons directed towards the anode per unit time.

The area of the anode irradiated by the electrons from the cathode is called the "focal spot" of the X-ray tube. In some X-ray analysis applications, in particular applications that require high resolution, it is preferable to have a small focal spot. In general, a smaller focal spot has a higher brilliance and can be used in an X-ray analysis apparatus to achieve relatively high efficiency at the detector.

Usually, when a small focal spot is required, an X-ray tube comprising a coiled tungsten filament is provided. Electrons are emitted by thermionic emission from the cathode, by resistively heating a filament. These X-ray tubes tend to have poor spectral stability when operated at low high-voltage settings (for example, less than 10 kV).

In order to maximise power at low high-voltage settings, the current applied to the filament must be increased (thereby increasing the emission current). However, this increases the amount of tungsten that is vaporized from the filament and deposited on the anode, which can prevent X-rays from being emitted by the anode. This can reduce the spectral stability of the X-ray tube.

In some other applications, X-ray tubes comprising a coated emission loop have been used. X-ray tubes comprising emission loops have only previously been used for applications that do not require high resolution, since these loops create large, annular shaped focal spots.

It would be desirable to provide a small X-ray tube that can achieve good performance in terms of providing small focal spot, high emission current at low high-voltage settings and good spectral stability (i.e. low output drift).

SUMMARY OF THE INVENTION

According to an aspect of the invention, there is provided an X-ray tube comprising an anode for emitting X-rays, the anode having a target surface; a cathode comprising an emission loop for emitting electrons, wherein the emission loop extends around an axis that passes through the anode, and the cathode and the anode are spaced apart from one another along the axis; and an electron beam guide configured to cause electrons emitted by the emission loop to irradiate an area of the target surface of the anode, wherein the area of the target surface irradiated by electrons is enclosed by a single boundary.

The electron beam guide is configured to influence the trajectory of the electrons from the cathode to the anode, so that the electrons irradiate a "solid" area of the anode, rather than a "hollow" area. More formally, the electron beam irradiates an area enclosed by a single boundary rather than an area enclosed by two separate boundaries (for example, an annulus is an area enclosed by two separate boundaries).

This arrangement facilitates the use of an emission loop to irradiate a small area of the anode. At the same time, the filament of the cathode is an emission loop, rather than a conventional coiled tungsten filament. Providing this arrangement can enable the X-ray tube to be operated at a high emission current with minimal impact on the output stability of the X-ray tube.

The largest linear dimension of the irradiated area of the anode may be between 0.1 mm and 2.0 mm, preferably between 0.9 mm and 1.5 mm. If the irradiated area is circular, the diameter of the irradiated area may be between 0.1 mm and 2.0 mm, preferably between 0.9 mm and 1.5 mm.

The X-ray tube may further comprise a first wall portion between the anode and the emission loop, wherein the first wall portion comprises a ring that extends around the axis.

In some embodiments, the ring is arranged to interrupt at least one direct line of sight from the emission loop to the anode so that, in use, electrons emitted by the emission loop travel along a curved trajectory from the emission loop to the anode.

In use, electrons emitted by the emission loop are accelerated towards the anode. The first wall portion interrupts the shortest path from the emission loop to the anode, so that the electrons take a curved trajectory. The anode and the emission loop are spaced apart from one another along the axis, so that the first wall portion partially blocks the anode. This arrangement helps to avoid the formation of a "hollow" focal spot. Providing this arrangement facilitates the formation of a small, solid focal spot.

The axis passes through the centre of an area enclosed by the first wall portion.

In some embodiments, the ring comprises an inclined outer surface which faces the emission loop, and the outer surface is inclined with respect to the axis so as to define an angle of between 30 degrees and 60 degrees between the outer surface and the axis, and preferably wherein the angle is between 40 degrees and 50 degrees.

In some embodiments, the outer surface of the first wall portion defines a frustoconical surface centred around the axis.

In some embodiments, the X-ray tube further comprises a housing that encloses the anode and the cathode, and the first wall portion is integrally formed with the housing.

The first wall portion forms part of an inner wall of the housing. Alternatively, the first wall portion can be separate from the housing. In some embodiments, the emission loop extends around the longitudinal axis of the housing. In these embodiments, the longitudinal axis passes through the target surface of the anode.

In some embodiments, the emission loop is centred on the axis and the angle between the target surface and a straight line extending from a point on the emission loop, through the centre of target surface is between 30 degrees and 60 degrees.

Preferably, the angle is between 40 degrees and 50 degrees. The distance between the target surface of the anode and the centre of the emission loop is equal to or less than 10 mm.

In some embodiments, the perimeter of the emission loop is larger than the perimeter of the target surface of the anode.

In some embodiments, the X-ray tube further comprises a second wall portion which extends around the axis, wherein the emission loop is arranged between the first wall portion and the second wall portion, and the second wall portion comprises an inclined inner surface that defines a tapered volume that tapers along the axis in a direction away from the anode, from the target surface of the anode.

The shape of the inner surface of the second wall portion can help to form a symmetrical focal spot. The tapered volume tapers in a direction from the anode, towards the emission loop.

The inner surface of the second wall portion may define a frustoconical surface that is centred around the axis.

In some embodiments, the X-ray tube further comprises a window for allowing X-rays to exit the X-ray tube, wherein the anode, the emission loop, and the window are spaced apart along the axis.

In some embodiments, the X-ray tube further comprises a third wall portion, wherein the third wall portion is annular, and the axis extends through the centre of the annulus.

In some embodiments, the annulus comprises an inner surface that faces the anode, wherein the inner surface extends in a plane parallel target surface of the anode.

In some embodiments, the emission loop is arranged between the third wall portion and the anode, in a direction along the axis.

The annulus may extend around a window of the X-ray tube. The emission loop and the third wall portion are centred around the axis, which passes through a target surface of the anode.

In some embodiments, the cathode comprises: a first wire of refractory metal extending between a first end and a second end, the first wire comprising the emission loop; a spiral of a second wire of refractory metal extending around and covering the first wire; and a coating covering the spiral of a second wire, the coating having a work function below 4 eV.

The coating can reduce the temperature at which the emission loop can emit electrons by thermionic emission. Providing this cathode can help to ensure that the X-ray tube can be operated at a high emission current with minimal impact on the output stability of the X-ray tube. In some embodiments, the coating is a barium oxide coating.

In an aspect of the invention, there is provided an X-ray tube comprising: an anode for emitting X-rays, the anode having an target surface; a cathode comprising an emission loop (11) for emitting electrons, wherein the emission loop extends around an axis that passes through the anode, and the cathode and the anode are spaced apart from one another along the axis (10); and an electron beam guide comprising a first wall portion (19) between the anode and the emission loop, wherein the first wall portion comprises a ring that extends around the axis, wherein the ring is arranged to interrupt at least one direct line of sight from the emission loop to the anode so that, in use, electrons emitted by the emission loop travel along a curved trajectory from the emission loop to the anode.

The electron beam guide is configured to influence the trajectory of the electrons from the cathode to the anode, so that the electrons irradiate a "solid" area of the anode, rather than a "hollow" area. More formally, the electron beam irradiates an area enclosed by a single boundary rather than an area enclosed by two separate boundaries (for example, an annulus is an area enclosed by two separate boundaries).

This arrangement facilitates the use of an emission loop to irradiate a small area of the anode. At the same time, the filament of the cathode is an emission loop, rather than a conventional coiled tungsten filament, which can enable the X-ray tube to be operated at a high emission current with minimal impact on the output stability of the X-ray tube.

The largest linear dimension of the irradiated area of the anode may be between 0.1 mm and 2.0 mm, preferably between 0.9 mm and 1.5 mm. If the irradiated area is circular, the diameter of the irradiated area may be between 0.1 mm and 2.0 mm, preferably between 0.9 mm and 1.5 mm.

The X-ray tube may further comprise a first wall portion between the anode and the emission loop, wherein the first wall portion comprises a ring that extends around the axis.

In some embodiments, the ring is arranged to interrupt at least one direct line of sight from the emission loop to the anode so that, in use, electrons emitted by the emission loop travel along a curved trajectory from the emission loop to the anode.

In use, electrons emitted by the emission loop are accelerated towards the anode. The first wall portion interrupts the shortest path from the emission loop to the anode, so that the electrons take a curved trajectory. The anode and the emission loop are spaced apart from one another along the axis, so that the first wall portion partially blocks the anode. This arrangement helps to avoid the formation of a "hollow" focal spot. Providing this arrangement facilitates the formation of a small, solid focal spot.

The axis passes through the centre of an area enclosed by the first wall portion.

In some embodiments, the ring comprises an inclined outer surface which faces the emission loop, and the outer surface is inclined with respect to the axis so as to define an angle of between 30 degrees and 60 degrees between the outer surface and the axis, and preferably wherein the angle is between 40 degrees and 50 degrees.

In some embodiments, the outer surface of the first wall portion defines a frustoconical surface centred around the axis.

In some embodiments, the X-ray tube further comprises a housing that encloses the anode and the cathode, and the first wall portion is integrally formed with the housing.

The first wall portion forms part of an inner wall of the housing. Alternatively, the first wall portion can be separate from the housing. In some embodiments, the emission loop extends around the longitudinal axis of the housing. In these embodiments, the longitudinal axis passes through the target surface of the anode.

In some embodiments, the emission loop is centred on the axis and the angle between the target surface and a straight line extending from a point on the emission loop, through the centre of target surface is between 30 degrees and 60 degrees.

Preferably, the angle is between 40 degrees and 50 degrees. The distance between the target surface of the anode and the centre of the emission loop is up to 10 mm.

In some embodiments, the perimeter of the emission loop is larger than the perimeter of the target surface of the anode.

In some embodiments, the X-ray tube further comprises a second wall portion which extends around the axis, wherein the emission loop is arranged between the first wall portion and the second wall portion, and the second wall portion comprises an inclined inner surface that defines a tapered volume that tapers along the axis in a direction away from the anode, from the target surface of the anode.

The shape of the inner surface of the second wall portion can help to form a symmetrical focal spot. The tapered volume tapers in a direction from the anode, towards the emission loop.

The inner surface of the second wall portion may define a frustoconical surface that is centred around the axis.

In some embodiments, the X-ray tube further comprises a window for allowing X-rays to exit the X-ray tube, wherein the anode, the emission loop, and the window are spaced apart along the axis.

In some embodiments, the X-ray tube further comprises a third wall portion, wherein the third wall portion is annular, and the axis extends through the centre of the annulus.

In some embodiments, the annulus comprises an inner surface that faces the anode, wherein the inner surface extends in a plane parallel target surface of the anode.

In some embodiments, the emission loop is arranged between the third wall portion and the anode, in a direction along the axis.

The annulus may extend around a window of the X-ray tube. The emission loop and the third wall portion are centred around the axis, which passes through a target surface of the anode.

In some embodiments, the cathode comprises: a first wire of refractory metal extending between a first end and a second end, the first wire comprising the emission loop; a spiral of a second wire of refractory metal extending around and covering the first wire; and a coating covering the spiral of a second wire, the coating having a work function below 4 eV.

The coating can reduce the temperature at which the emission loop can emit electrons by thermionic emission. Providing this cathode can help to ensure that the X-ray tube can be operated at a high emission current with minimal impact on the output stability of the X-ray tube. In some embodiments, the coating is a barium oxide coating.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides an X-ray tube having a cathode and an anode. The cathode comprises an emission loop for emitting electrons. The X-ray tube also includes an electron beam guide configured to cause electrons from the emission loop to irradiate an area of an anode that is enclosed by a single boundary (a solid area). Cathodes comprising emission loops have previously only been used to form large, hollow focal spots (having a diameter of roughly 12 mm, for example).

Figure 1:
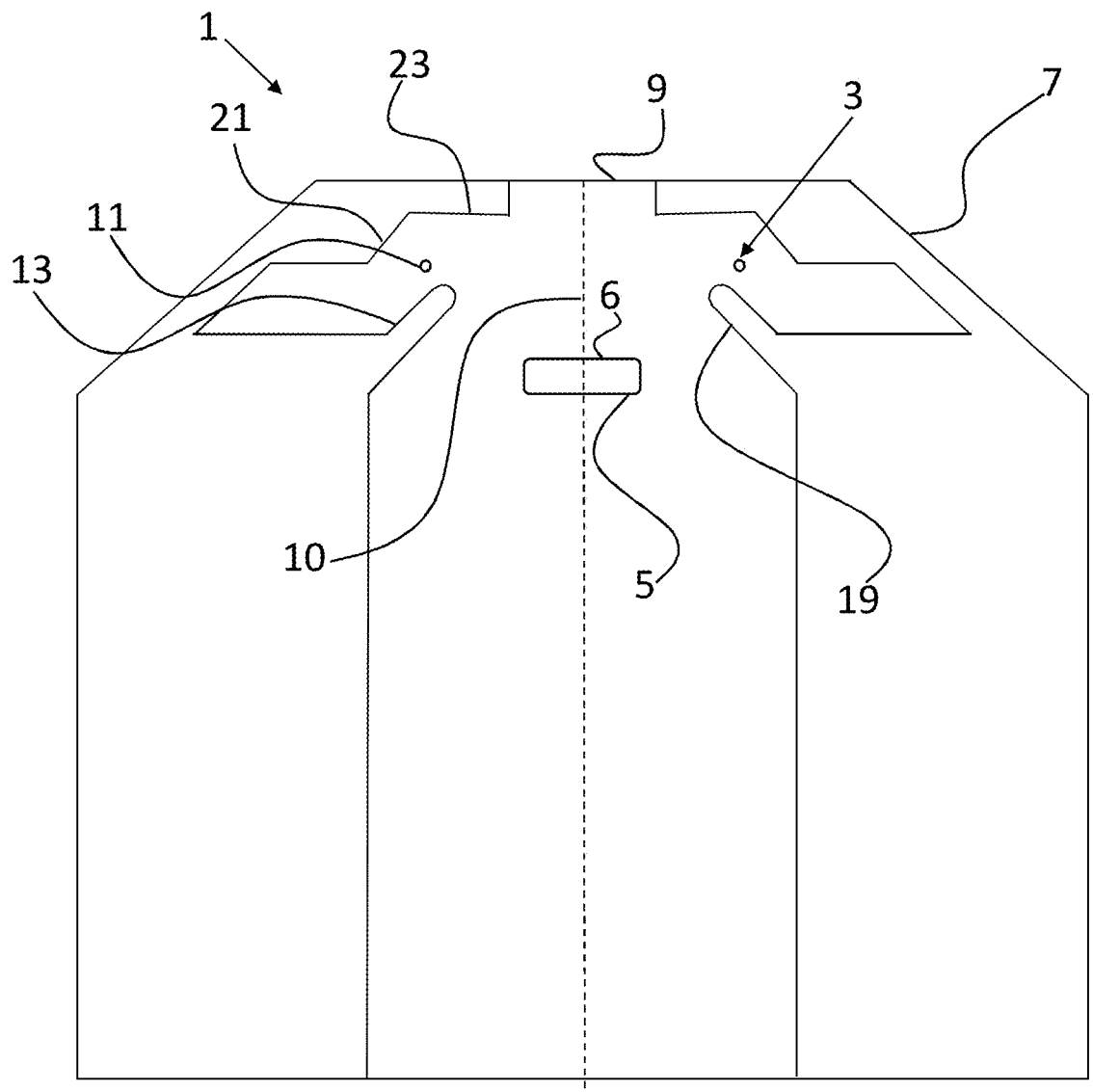
FIG. 1 shows a schematic cross sectional view of an X-ray tube according to an embodiment of the invention.

FIG. 1 shows an X-ray tube 1 in cross section. The X-ray tube 1 comprises a cathode 3 and an anode 5, which are arranged in a housing 7. The housing 7 provides a vacuum tube. In use, the cathode 3 is heated and emits electrons by thermionic emission. Electrons from the cathode 3 form an electron beam, which is directed towards a target surface 6 of the anode 5. A high voltage is applied to the anode 5 while the cathode 3 is held at ground, so that there is a potential difference between the anode 5 and the cathode 3. Electrons from the cathode 3 accelerate towards the anode 5. When electrons from the cathode 3 hit the anode 5, they cause X-rays to be emitted from the anode 5. The emitted X-rays pass out of the X-ray tube 1, through a window 9 in the tube 1. The window is arranged at an end of the X-ray tube, facing the target surface 6 of the anode 5. The cathode is arranged between the anode 5 and the window 9.

In FIG. 1, the housing 7 has a longitudinal axis 10. The cathode 3 and anode 5 are spaced apart from one another in a direction along the longitudinal axis 10 of the vacuum tube 7. The cathode 3 comprises an emission loop 11, which extends around the longitudinal axis 10 so that the emission loop 11 is centred on the axis 10. The perimeter of the emission loop is larger than the perimeter of the target surface 6, so that the emission loop 11 also extends around the target surface 6 of the anode 5. The longitudinal axis 10 passes through the target surface 6 of the anode 5, through the centre of the emission loop 11, and through the window 9.

The electrons emitted by the emission loop are guided by an electron beam guide, which at least partly determines the path taken by the electrons from the cathode to the anode.

In the embodiment shown in FIG. 1, the electron beam guide is provided by an inner wall of the housing 7. The inner wall is shaped so that, in use, the electric field inside the X-ray tube 1 directs electrons emitted from the cathode 3 towards the target surface 6 of the anode 5 to irradiate a solid area of the target surface (rather than a hollow area). The shape of the inner wall influences the electric field inside the X-ray tube, and therefore influences the trajectory of electrons emitted by the cathode 3. During operation, the inner wall is held at ground while a high voltage is applied to the anode 5.

The inner wall of the X-ray tube comprises a first wall portion 19. The first wall portion is arranged between the emission loop 11 and the anode 5, so as to physically block the shortest straight path from the emission loop to the target surface 6 of the anode 5. The first wall portion 19 comprises an outer surface 13, which faces outwardly from the axis 10 and towards the emission loop 11. The outer surface is inclined with respect to the axis 10. In FIG. 1, the outer surface is at an angle of 45 degrees to the axis 10. In this arrangement, the first wall portion 19 partially blocks the target surface 6 of the anode from the emission loop. Electrons emitted by the emission loop are forced to curve over the first wall portion 19 before they arrive at the target surface 6 of the anode. Because the anode is spatially separated from the emission loop along the axis 10, the electrons travel towards the target surface along an extended path. This can help to reduce the size of the irradiated area of the anode.

The inner wall also includes a second wall portion 21 which is arranged between the first wall portion and the window 9, in a direction along the axis 10. The second wall portion comprises a ring that extends around the axis 10. An inner surface of the second wall portion is inclined, and defines a tapered volume, which tapers in a direction from the target surface 6 of the anode 5 towards the window 9.

A third wall portion of the inner wall encircles the window 9 to define a neck of the X-ray tube. The second wall portion 21 of the inner wall of the X-ray tube is arranged under the third wall portion.

Together, the second wall portion and the third wall portion define a shoulder, which extends from the neck, over the cathode 3. The lower surface of the third wall portion, which faces the anode, defines the upper part of the shoulder and the inner surface of the second wall portion 21 provides the lower part of the shoulder of the inner wall.

Below the shoulder, and under the cathode, the first wall portion of the inner wall projects inwardly, towards the axis, and upwardly, away from the target surface of the anode.

Figure 2A:
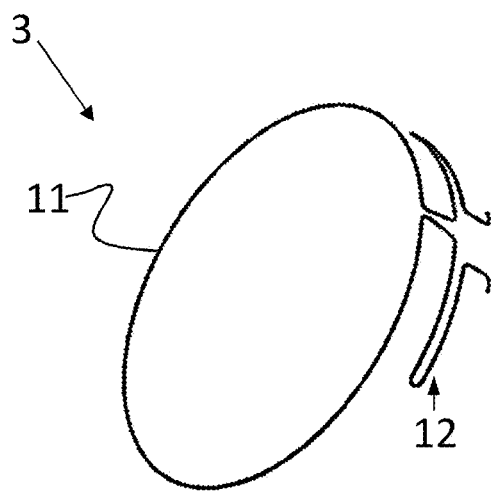
FIG. 2A shows a perspective view of a cathode comprising an emission loop.

Turning to FIG. 2A, the cathode 3 is shown in more detail. The cathode 3 comprises a single length of tungsten wire extending between a first end and a second end which are arranged adjacently. The cathode has the form of a circular emission loop 11 with first and second thermal loops 12 formed between the emission loop 11 and the first and second end. Each of the first and second thermal loops is formed of a U-shaped loop of wire, the legs of the U extending in parallel to the emission loop, that is to say following the circle. The term "thermal loop" is used since the function of the loop is to provide some thermal resistance between the emission loop and the ends of the wire.

Figure 2B:
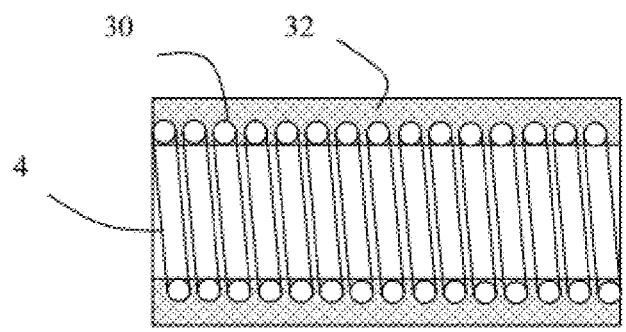
FIG. 2B shows a close up view of the emission loop.

FIG. 2B shows the emission loop in more detail. The cathode comprises a first tungsten wire 4, which forms the circular emission loop, a second tungsten wire 30 and an emitter coating 32. The second tungsten wire 30 is arranged in a spiral, around the first tungsten wire 4. The emitter coating 32 is arranged on the composition of wires. In the example, there are small gaps between individual turns of the spiral wire, and the coating extends into these gaps as well as over the surface. This is believed to create a strong bond and good chemical contact between the coating 32 and wires 4, 30.

The emission loop has a maximum linear dimension (i.e. diameter in the case of a circle), from 0.5 mm to 5 mm. The coating thickness may be from 0.5 μm to 50% of the diameter of the emission loop. The second wire may be tightly bound to the first wire, or may be spaced from it, for example from 0 to 20% of the diameter of the emission loop. The support wire may be, for example, from 20 to 500 μm diameter and any suitable length, for example from 2 mm to 30 mm. The support wire may in particular have a diameter 20% to 80%, or 20% to 50% of that of the inner wire.

The emitter coating 32 comprises a material that results in thermionic emission at a lower temperature than that of tungsten. For example, the coating comprises Barium oxide and/or Strontium Oxide. The coated emission loop 11 provides electron emission at lower temperatures, so that evaporation of material is reduced or avoided. Therefore, the cathode can achieve stable X-ray output over time.

The cathode delivers a very even X-ray spot, because of the even temperature distribution and good bonding between the coating and the coiled wire.

The inventors have realised that by providing an X-ray tube 1 comprising an emission loop that is provided above the anode, it is possible to provide a full/solid (i.e. not hollow) focal spot and at the same time achieve high output stability at low high-voltage settings.

Table 1 shows some low kV settings for an X-ray tube according to the present invention, as well as for two comparative X-ray tubes. One of the comparative X-ray tubes has an uncoated tungsten filament in the form of a coil. It can be seen that the lowest kV setting for the comparative X-ray tube, without unacceptable output drift, is 10 kV. At this low high-voltage setting, power is limited to 500 W, to preserve the lifetime of the cathode. Note, also, that the focal spot using the 12 mm emission loop is annular.

The X-ray tube according to the present invention can also be used at higher mA settings. For example, it is possible to operate at currents of up to 12 mA whilst still achieving good spectral stability.

TABLE 1

| X-ray Tube Operation Settings | | | | | |
|---|---|---|---|---|---|
| | X-ray tube operation settings | | | Focal spot | |
| X-ray Tube | kV | mA | W | size (mm) | Drift |
| Embodiment | 4 | 5 | 20 | 1 to 1.5 | Low |
| Comparative X-ray tube (uncoated filament) | 4.5 | 3 | 13.5 | 1 to 1.5 | Medium/High |
| Comparative X-ray tube (emission loop) | 10 | 50 | 500 | 12 | Low |

Figure 3:
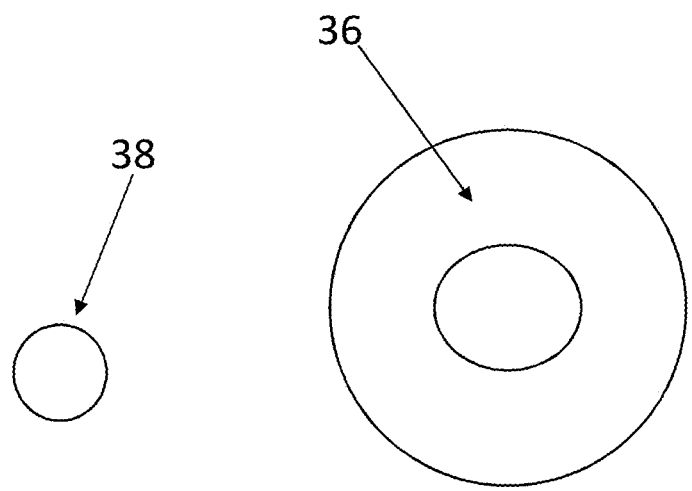
FIG. 3 illustrates an example "ring shaped" focus and a "spot shaped" focus.

FIG. 3 shows an annular focal spot 36 and a solid focal spot 38. The annular focal spot has a hollow shape, defined between two distinct boundaries. Previously, X-ray tubes using emission loops produce focal spots of this shape. These focal spots are large (typically around 12 mm in diameter).

The solid focal spot in FIG. 3 is enclosed by a single continuous boundary. It is not hollow. It has a diameter of 1.5 mm.

Figure 4:
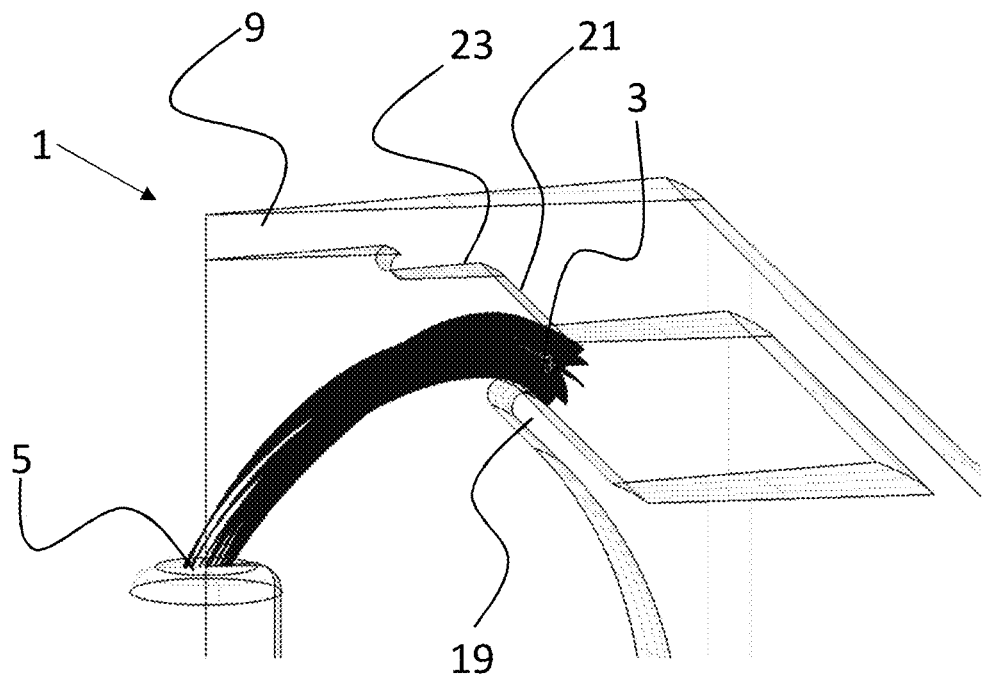
FIG. 4 illustrates the path of an electron beam in the X-ray tube of FIG. 1.

FIG. 4 is a schematic depiction of the path of the electron beam for the X-ray tube 1 of FIG. 1, in use. As show in FIG. 4, in use, electrons are emitted from the cathode 3 and travel towards anode 5 under the influence of the electric field within the X-ray tube 1. The electron beam guide is arranged to shape the beam of electrons from the cathode, so that the electrons irradiate a solid area of the target surface 6 of the anode 5. The inner wall is shaped so that electrons from the cathode are forced to take a curved trajectory over the first wall portion. The shape of the inner wall can help to ensure that the electrons from the cathode spread out over the anode, so that the electrons irradiate a solid area on the surface of the anode. As shown in FIG. 4, electrons from the cathode 3 are directed towards the anode 5 and irradiate an area of the anode enclosed by a single boundary.

Figure 5:
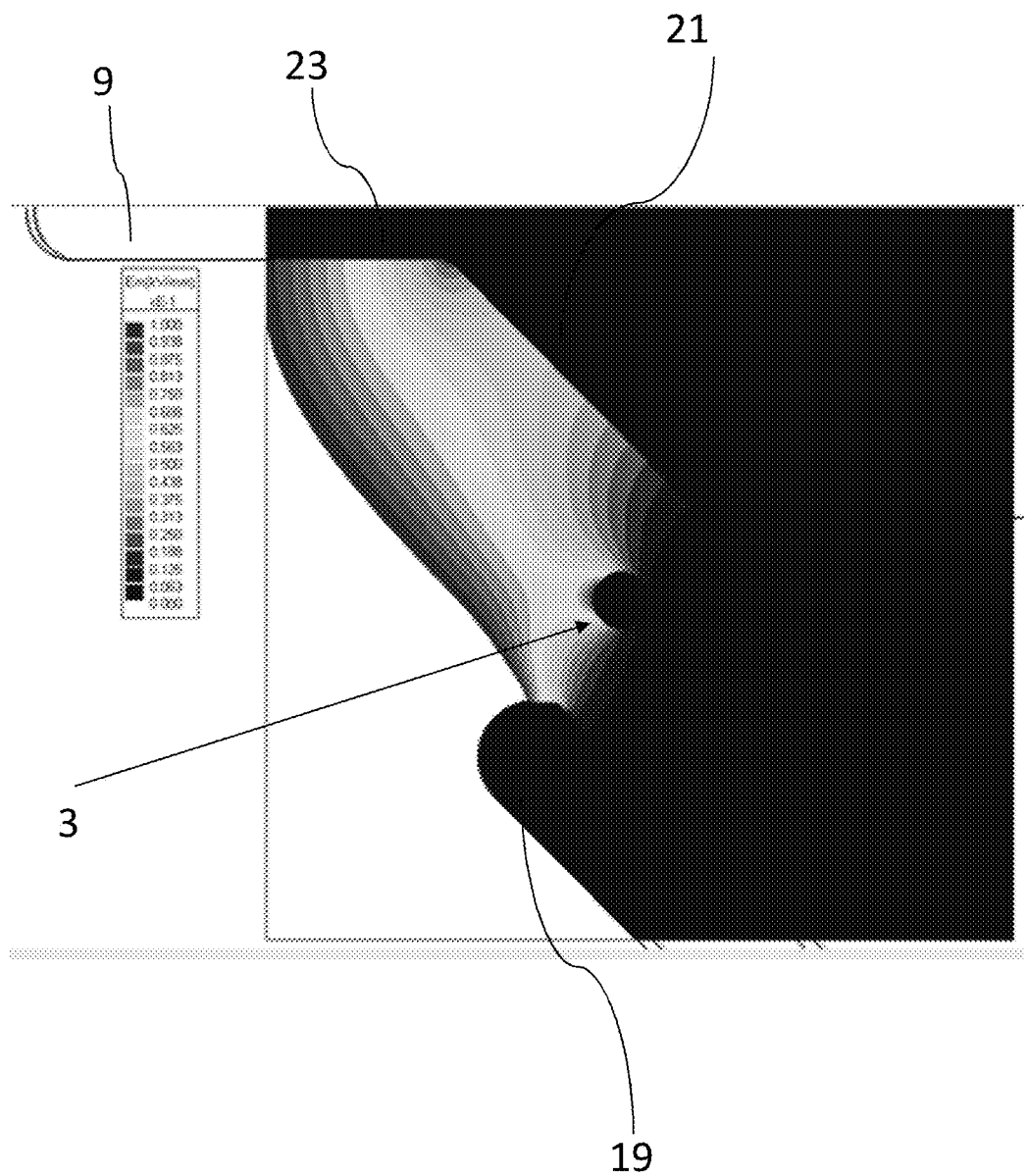
FIG. 5 illustrates the electric field inside the X-ray tube, according to an embodiment.

FIG. 5 shows the electric field inside the X-ray tube 1, when the X-ray tube 1 is in use.

Figure 6:
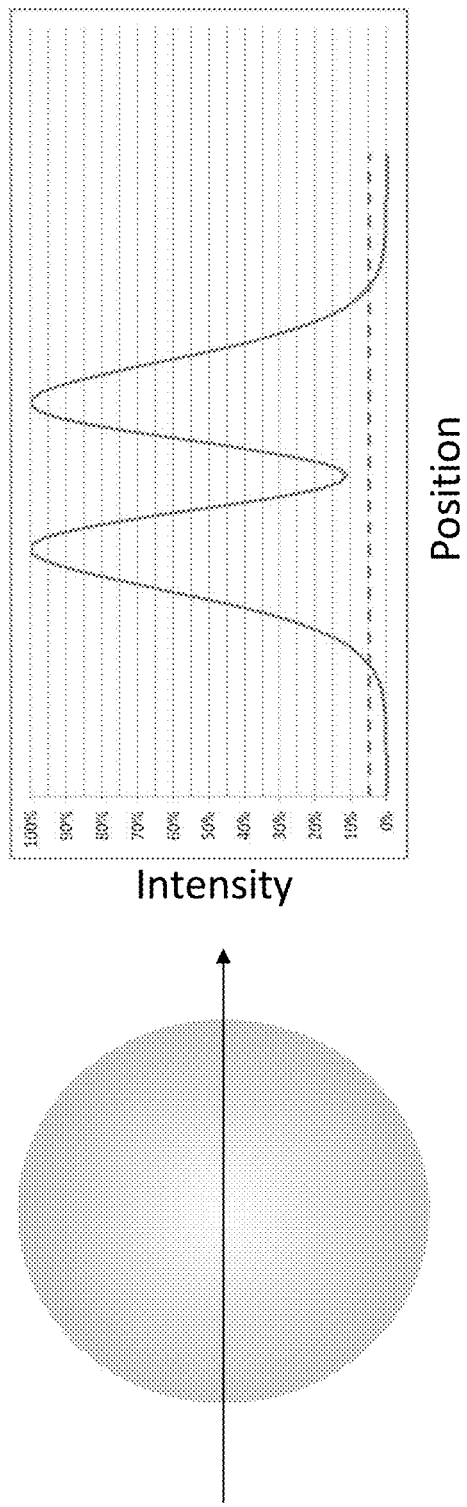
FIG. 6 shows intensity variation with position for an exemplary irradiated area of the anode.

FIG. 6 illustrates how the intensity of a focal area varies with position. This can be used to determine whether a focal area is "solid" (an area enclosed by a single boundary) or "hollow" (an area enclosed by more than one boundary). It is possible to determine the shape of the focal area by capturing an image of the anode and processing the image to assess the shape of the focal area.

The parts of the anode irradiated by electrons will have a higher intensity in the image of the anode. One way to determine whether the central region of an area of the anode is irradiated by electrons is to analyse an image of the anode.

For example, an area of the anode enclosed by a single boundary is selected. The selected area encloses the focal area. The peak intensity of the selected area is determined. Then, the average intensity of the central region of the selected area is determined. For example, the central region is a region in the centre of the selected area that is equal to approximately 10% of the total selected area. If the average intensity of the central region is equal to or less than 5% of the peak intensity, the focal area is a hollow focal area. If the average intensity of the central region is greater than 5% of the peak intensity, the focal area is a solid focal area.

In FIG. 6, the image of the selected area of the anode 61 is shown on the left hand side of the page. The graph on the right hand side of the page shows how the measured intensity changes with position on the image of the selected area of the anode. In this example, the central region has an intensity that is greater than 5% of the peak intensity. Accordingly, the focal area is a "solid" focal area.

In some embodiments, the first wall portion is a ring. The ring is not necessarily circular.

In some embodiments, the cathode does not comprise any thermal loops.

In some embodiments, the first wall portion is not integrally formed with the housing. That is the first wall portion is a separate entity to the housing.

In some embodiments, the first wall portion and the second wall portion are separate entities. In other embodiments, the first wall portion and the second wall portion are integrally formed.

In some embodiments, the second wall portion and the third wall portion are separate entities. In other embodiments, the second wall portion and the third wall portion are integrally formed.

In some embodiments, the electron beam guide is provided by the inner surface of the vacuum tube. In other embodiments, the electron beam guide is separate to the vacuum tube.

The area of the anode irradiated by the electron beam may be circular, or it may have a different shape. For example, the area irradiated by the electron beam may be elliptical.

The anode may be of any material suitable for producing X-rays.

The skilled person will understand that an X-ray tube may not be strictly tubular.

The invention claimed is:

1. An X-ray tube comprising:
    an anode for emitting X-rays, the anode having a target surface;
    a cathode comprising an emission loop for emitting electrons, wherein the emission loop extends around an axis that passes through the anode, and the anode and the cathode are spaced apart from one another along the axis; and
    an electron beam guide configured to cause electrons emitted by the emission loop to irradiate an area of the target surface of the anode, wherein the area of the target surface irradiated by electrons is enclosed by a single boundary, wherein the emission loop is centred on the axis and the angle between the target surface and a straight line extending from a point on the emission loop, through the centre of the target surface is between 30 degrees and 60 degrees.

2. The X-ray tube of claim 1 further comprising a first wall portion between the anode and the emission loop, wherein the first wall portion comprises a ring that extends around the axis.

3. The X-ray tube of claim 2, wherein the ring is arranged to interrupt at least one direct line of sight from the emission loop to the anode so that, in use, electrons emitted by the emission loop travel along a curved trajectory from the emission loop to the anode.

4. The X-ray tube of claim 3, wherein the ring comprises an inclined outer surface which faces the emission loop, and the outer surface is inclined with respect to the axis so as to define an angle of between 30 degrees and 60 degrees between the outer surface and the axis.

5. The X-ray tube of claim 3, wherein the ring comprises an inclined outer surface which faces the emission loop, and the outer surface is inclined with respect to the axis so as to define an angle of between 40 degrees and 50 degrees between the outer surface and the axis.

6. The X-ray tube of claim 2, wherein the outer surface of the first wall portion defines a frustoconical surface centred around the axis.

7. The X-ray tube of claim 2 further comprising a housing that encloses the anode and the cathode, and the first wall portion is integrally formed with the housing.

8. The X-ray tube of claim 2 further comprising a second wall portion which extends around the axis, wherein the emission loop is arranged between the first wall portion and the second wall portion, and the second wall portion comprises an inclined inner surface that defines a tapered volume that tapers along the axis in a direction away from the anode, from the target surface of the anode.

9. The X-ray tube of claim 1, wherein the perimeter of the emission loop is larger than the perimeter of the target surface of the anode.

10. The X-ray tube of claim 1 further comprising a window for allowing X-rays to exit the X-ray tube, wherein the anode, the emission loop, and the window are spaced apart along the axis.

11. The X-ray tube of claim 9 further comprising a third wall portion, wherein the third wall portion is annular, and the axis extends through the centre of the annulus.

12. The X-ray tube of claim 11, wherein the annulus comprises an inner surface that faces the anode, wherein the inner surface extends in a plane parallel target surface of the anode.

13. The X-ray tube of claim 11, wherein the emission loop is arranged between the third wall portion and the anode, in a direction along the axis.

14. The X-ray tube of claim 1, wherein the cathode comprises:
    a first wire of refractory metal extending between a first end and a second end, the first wire comprising the emission loop;
    a spiral of a second wire of refractory metal extending around and covering the first wire; and
    a coating covering the spiral of a second wire, the coating having a work function below 4 eV.

15. An X-ray tube comprising:
    an anode for emitting X-rays, the anode having a target surface;
    a cathode comprising an emission loop for emitting electrons, wherein the emission loop extends around an axis that passes through the anode, and the cathode and the anode are spaced apart from one another along the axis; and an electron beam guide comprising a first wall portion between the anode and the emission loop, wherein the first wall portion comprises a ring that extends around the axis, wherein the ring is arranged to interrupt at least one direct line of sight from the emission loop to the anode so that, in use, electrons emitted by the emission loop travel along a curved trajectory from the emission loop to the anode, wherein the emission loop is centred on the axis and the angle between the target surface and a straight line extending from a point on the emission loop, through the centre of the target surface is between 30 degrees and 60 degrees.

\* \* \* \* \*